United States Patent
Wang et al.

(10) Patent No.: US 9,169,181 B2
(45) Date of Patent: Oct. 27, 2015

(54) PRODUCTION OF CYCLOHEXYLBENZENE HYDROPEROXIDE

(75) Inventors: Kun Wang, Bridgewater, NJ (US); Edmund John Mozeleski, Somerset, NJ (US); Jihad Mohammed Dakka, Whitehouse Station, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/007,281

(22) PCT Filed: Nov. 28, 2011

(86) PCT No.: PCT/US2011/062200
§ 371 (c)(1),
(2), (4) Date: Jul. 3, 2014

(87) PCT Pub. No.: WO2012/134549
PCT Pub. Date: Oct. 4, 2012

(65) Prior Publication Data
US 2014/0316166 A1    Oct. 23, 2014

Related U.S. Application Data

(60) Provisional application No. 61/468,290, filed on Mar. 28, 2011.

(30) Foreign Application Priority Data

May 31, 2011  (EP) .................................. 11168156

(51) Int. Cl.
C07C 45/53 (2006.01)
C07C 407/00 (2006.01)
C07C 37/08 (2006.01)

(52) U.S. Cl.
CPC ............... C07C 37/08 (2013.01); C07C 45/53 (2013.01); C07C 407/00 (2013.01); C07C 407/003 (2013.01); C07C 2101/14 (2013.01)

(58) Field of Classification Search
CPC ........ C07C 45/53; C07C 37/08; C07C 409/14
USPC ........................ 568/356, 568, 798; 585/467
See application file for complete search history.

(56) References Cited

U.S. PATENT DOCUMENTS

| | | | |
|---|---|---|---|
| 3,821,314 A | 6/1974 | Arkell et al. | |
| 3,856,661 A | 12/1974 | Sugier et al. | |
| 3,959,381 A | 5/1976 | Arkell et al. | |
| 4,282,383 A | 8/1981 | Dai et al. | |
| 4,439,409 A | 3/1984 | Puppe et al. | |
| 4,826,667 A | 5/1989 | Zones et al. | |
| 4,954,325 A | 9/1990 | Rubin et al. | |
| 5,236,575 A | 8/1993 | Bennett et al. | |
| 5,250,277 A | 10/1993 | Kresge et al. | |
| 5,362,697 A | 11/1994 | Fung et al. | |
| 6,037,513 A | 3/2000 | Chang et al. | |
| 6,077,498 A | 6/2000 | Diaz Cabanas et al. | |
| 6,201,157 B1 | 3/2001 | Keenan | |
| 6,756,030 B1 | 6/2004 | Rohde et al. | |
| 7,285,684 B2 | 10/2007 | Miura et al. | |
| 8,598,388 B2 * | 12/2013 | Bencini et al. | 568/342 |

FOREIGN PATENT DOCUMENTS

| | | |
|---|---|---|
| CN | 1490293 | 4/2004 |
| EP | 0 293 032 | 11/1988 |
| EP | 2 098 504 | 9/2009 |
| WO | WO 97/17290 | 5/1997 |
| WO | WO 2009/025939 | 2/2009 |
| WO | WO 2010/074779 | 7/2010 |
| WO | WO2011/001244 A1 * | 1/2011 |
| WO | WO 2012/036824 | 3/2012 |
| WO | WO 2012/036825 | 3/2012 |

OTHER PUBLICATIONS

Zakoshansky, V.M., "Phenol Process Trends; Section II—Technical Grade Cumene Hydroperoxide Cleavage", ILLA International, LLC, 4756 Doncaster Court, Long Grouve, IL 60047-6929, pp. 1-13.

* cited by examiner

Primary Examiner — Sikarl Witherspoon
(74) Attorney, Agent, or Firm — Siwen Chen; Stephen A. Baehl

(57) ABSTRACT

In a process for producing cyclohexylbenzene hydroperoxide, cyclohexylbenzene is contacted with oxygen to produce a reaction product comprising cyclohexylbenzene hydroperoxide and unreacted cyclohexylbenzene. The reaction product is then maintained under conditions such that crystals of cyclohexylbenzene hydroperoxide form and separate from the reaction product. The cyclohexylbenzene hydroperoxide crystals are then recovered from the reaction product.

21 Claims, No Drawings

PRODUCTION OF CYCLOHEXYLBENZENE HYDROPEROXIDE

PRIORITY CLAIM TO RELATED APPLICATIONS

This application is a National Stage Application of International Application No. PCT/US2011/062200 filed Nov. 28, 2011, which claims priority to U.S. Provisional Application Ser. No. 61/468,290 filed Mar. 28, 2011, and European Application No. 11168156.5 filed May 31, 2011, the disclosures of which are fully incorporated herein by their reference.

CROSS REFERENCE TO RELATED APPLICATIONS

This application is related to U.S. application Ser. No. 13/122,608 filed Sep. 17, 2009 (2008EM334), International Patent Cooperation Treaty Application Nos. PCT/US2011/047843 (2011EM115) and PCT/US2011/047840 (2011EM122), both filed Aug. 16, 2011.

FIELD

The present invention relates to a process for producing cyclohexylbenzene hydroperoxide and, in particular, to a process for producing cyclohexylbenzene hydroperoxide and then cleaving the resultant cyclohexylbenzene hydroperoxide to produce phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process involving alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene. Thus, a process that does not require propylene as a feed and coproduces higher ketones, rather than acetone, may be an attractive alternative route to the production of phenol.

One such process involves the catalytic hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Such a process is described in, for example, U.S. Pat. No. 6,037,513, in which the hydroalkylation catalyst is a bifunctional catalyst comprising at least one hydrogenation metal and a molecular sieve of the MCM-22 family.

However, one problem in producing phenol via cyclohexylbenzene is that the oxidation of cyclohexylbenzene is considerably more difficult than that of cumene. Thus, whereas cumene oxidation is normally conducted in the absence of a catalyst, cyclohexylbenzene oxidation typically requires the presence of a catalyst containing a nitroxyl radical, such as N-hydroxyphthalimide (NHPI), to provide commercially acceptable levels of conversion. However, even using NHPI as a catalyst, the selectivity to cyclohexylbenzene hydroperoxide decreases with increasing conversion. Thus the product of the cyclohexylbenzene oxidation step typically contains large amounts (of the order of 80 wt %) of unreacted cyclohexylbenzene as well as significant quantities of impurities. If these materials are allowed to pass to the ensuing cleavage step, not only can they generate expensive separation problems but also some of the impurities may be converted in the cleavage process to produce tars and thereby reduce the yield of phenol and cyclohexanone.

There is therefore significant incentive to concentrate/isolate the cyclohexylbenzene hydroperoxide after the oxidation step. Thus, using pure or high concentrated of cyclohexylbenzene hydroperoxide in the cleavage step may reduce tar/by-product formation during cleavage and will also reduce the volume of cyclohexylbenzene that needs to be treated and handled after the cleavage step. However, whereas cumene hydroperoxide can readily be concentrated by distillation, the high boiling point of cyclohexylbenzene (240° C.) means that concentration of cyclohexylbenzene hydroperoxide by distillation requires high temperatures and/or high vacuum, which can lead to thermal decomposition of the hydroperoxide. Thus alternative methods of concentrating and/or purifying cyclohexylbenzene hydroperoxide would be desirable.

According to the present invention, it has now been found that high purity cyclohexylbenzene hydroperoxide can be recovered from the reaction product of cyclohexylbenzene oxidation by selective crystallization. After separation from the mother liquor, the resultant cyclohexylbenzene hydroperoxide crystals can be redissolved in a solvent, such as acetone, and then fed to the cleavage step.

U.S. Pat. No. 3,821,314 discloses a process for the separation of cyclohexylbenzene hydroperoxide from a mixture of cyclohexylbenzene and its oxidation products by adsorption of the oxidation products with a polyurethane foam. The oxidation products can then be separated selectively from the foam by elution with a non-polar hydrocarbon solvent, such as pentane.

U.S. Pat. No. 3,959,381 discloses a two-stage process for purifying cyclohexylbenzene hydroperoxide produced by the oxidation of cyclohexylbenzene, in which the oxidation effluent is initially subjected to vacuum distillation at a temperature between ambient and 90° C. and a pressure between about 0.1 and 0.5 mm Hg to remove at least part of the unreacted cyclohexylbenzene. The distillation residue is then treated with a lower ($C_5$ to $C_{10}$) liquid alkane to separate the cyclohexylbenzene hydroperoxide as extract from the oxidation by-products.

U.S. Pat. No. 7,285,684 discloses a process for separating a reaction product and an imide compound having an imide unit represented by the following formula:

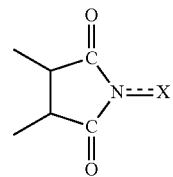

wherein X represents an oxygen atom, a hydroxyl group, or an acyloxy group, which process comprises separating the imide compound from the reaction mixture by solvent-crystallizing the imide compound with water or a mixture of water and at least one solvent selected from the group consisting of a hydrocarbon and a chain ether, or, when the reaction mixture is obtained by an oxidation reaction of a monocyclic $C_4$-$C_{16}$ cycloalkane substrate, with at least one solvent selected from the group consisting of a hydrocarbon and a chain ether.

SUMMARY

In one aspect, the invention resides in a process for producing cyclohexylbenzene hydroperoxide, the process comprising:

(a) contacting cyclohexylbenzene with oxygen and an oxidation catalyst to produce a reaction product comprising cyclohexylbenzene hydroperoxide and at least a portion of the oxidation catalyst;

(b) treating the reaction product under conditions such that crystals of cyclohexylbenzene hydroperoxide form; and (c) recovering at least a portion of the cyclohexylbenzene hydroperoxide crystals.

In one embodiment, the oxidation catalyst is a cyclic imide and the process further comprises treating the reaction product to remove at least part of the oxidation catalyst from the reaction product prior to step (b).

Conveniently, the reaction product is treated with an aqueous solution of a base, such as a metal carbonate and/or hydrogen carbonate, to remove at least part of the catalyst from the reaction product.

Alternatively, the reaction product is treated with a solid sorbent to remove at least part of the oxidation catalyst from the reaction product. Conveniently, the solid sorbent is selected from alkali metal carbonates, alkali metal bicarbonates, alkali metal hydroxides, alkali metal hydroxide-carbonate complexes, alkaline earth metal carbonates, alkaline earth metal bicarbonates, alkaline earth metal hydroxides, and alkaline earth metal hydroxide-carbonate complexes.

Conveniently, step (b) comprises cooling the treated reaction product to a temperature between about 2° C. and about 10° C.

Conveniently, the oxidation catalyst comprises an imide group having the formula:

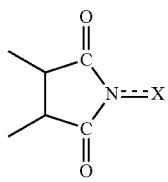

wherein X represents an oxygen atom, a hydroxyl group, or an acyloxy group.

In one embodiment, the catalyst comprises N-hydroxyphthalimide.

Conveniently, the process further comprises using the cyclohexylbenzene hydroperoxide recovered in (c) as an oxidant or as an initiator.

In a further aspect, the invention resides in a process for producing phenol and cyclohexanone, the process comprising:

(a) contacting cyclohexylbenzene with oxygen and N-hydroxyphthalimide to produce a reaction product comprising cyclohexylbenzene hydroperoxide and at least a portion of the N-hydroxyphthalimide;

(b) treating the reaction product under conditions such that crystals of cyclohexylbenzene hydroperoxide form;

(c) recovering at least a portion of the cyclohexylbenzene hydroperoxide crystals; and (d) cleaving at least part of the cyclohexylbenzene hydroperoxide recovered in (c) to produce phenol and cyclohexanone.

Conveniently, at least part of the cyclohexylbenzene is formed by reacting benzene with hydrogen.

DESCRIPTION

Described herein is a process for producing cyclohexylbenzene hydroperoxide, in which cyclohexylbenzene is contacted with oxygen, normally in the presence of a cyclic imide catalyst to produce a liquid reaction product comprising cyclohexylbenzene hydroperoxide, imide catalyst, and potentially unreacted cyclohexylbenzene. If necessary, the reaction product is then treated to remove at least part of any imide catalyst from reaction product, whereafter the treated reaction product is subjected to conditions such that the cyclohexylbenzene hydroperoxide crystallizes and the resultant cyclohexylbenzene hydroperoxide crystals separate from the treated reaction product and can be recovered, for example by filtration or centrifuging.

In one preferred embodiment, the present oxidation process forms part of an integrated process for producing phenol and cyclohexanone from benzene, in which the benzene is converted to cyclohexylbenzene, the cyclohexylbenzene is then oxidized to cyclohexylbenzene hydroperoxide and the cyclohexylbenzene hydroperoxide is cleaved to produce phenol and cyclohexanone. The present process will therefore be described in relation to this preferred embodiment, although it is to be appreciated that the cyclohexylbenzene hydroperoxide product of the present process can also be used as an oxidant in, for example, the oxidation of hydrocarbons, or as an initiator, in, for example, olefin polymerization (e.g., epoxification).

Production of the Cyclohexylbenzene

The initial step in the integrated process involves the production of cyclohexylbenzene by reacting benzene with cyclohexene in the presence of a catalyst having an alkylation function and under conditions to promote the following reaction:

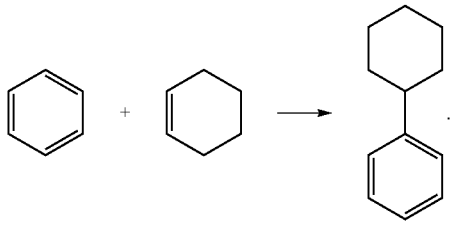 [SMILES: c1ccccc1 ; C1=CCCCC1 ; c1ccc(C2CCCCC2)cc1]

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

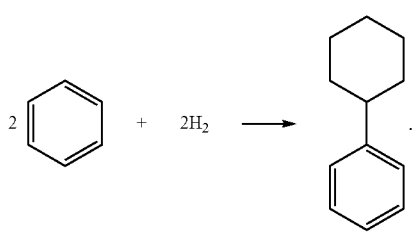 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Treatment of the Cyclohexylbenzene Product

Although the hydroalkylation reaction using an MCM-22 family zeolite catalyst is highly selective towards cyclohexylbenzene, the liquid effluent from the hydroalkylation reaction will inevitably contain significant quantities of unreacted benzene and certain by-products in addition to the desired cyclohexylbenzene. One of the major by-products are polycyclohexylbenzenes (di- and tricyclohexylbenzene), which typically comprise up to 20 wt % of the conversion products. Thus, for the overall process to be economically feasible, it is necessary to convert these polycyclohexylbenzenes into additional useful cyclohexylbenzene product. This can be achieved by transalkylation or dealkylation, but initially it is necessary to separate the polycyclohexylbenzenes from the reaction product.

In the present process, separation of the polycyclohexylbenzenes is achieved by supplying at least a portion of the reaction product to a fractionation device, normally a fractionation column, to separate the reaction product into at least a first fraction rich in cyclohexylbenzene and a second fraction rich in polycyclohexylbenzenes. In addition, to allow the separation to be effected at or near atmospheric pressure (about 100 kPa to about 300 kPa) and at relatively low temperatures, at least one $C_4$ to $C_6$ hydrocarbon in the vapor phase is supplied separately to the fractionation device, normally at or adjacent the base of the fractionation column. Although any $C_4$ to $C_6$ hydrocarbon vapor can be used, benzene vapor is particularly useful since, for example, the hydroalkylation reaction effluent contains significant quantities (typically up to 60 wt %) of unreacted benzene.

Conveniently, the $C_4$ to $C_6$ hydrocarbon vapor is supplied to the fractionation device in (c) at a temperature of about 190° C. to about 300° C. More particularly, where steam is used to heat and vaporize the $C_4$ to $C_6$ hydrocarbon, the temperature of the $C_4$ to $C_6$ hydrocarbon vapor supplied to the fractionation device in (c) is between about 190° C. and about 241° C. Generally, the ratio of the weight of the $C_4$ to $C_6$ hydrocarbon vapor supplied to the fractionation device to the weight of the reaction product supplied to the fractionation device is from about 0.05:1 to about 2:1, such as from about 0.1:1 to about 1:1, for example about 0.5:1.

In one embodiment of the present process, after separation from the hydroalkylation reaction effluent, the polycyclohexylbenzenes are mixed with benzene and transalkylated to produce additional monocyclohexylbenzene. Transalkylation is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr$^{-1}$ on total feed, and a benzene/dicyclohexylbenzene weight ratio about of 1:1 to about 5:1.

In another embodiment of the present process, conversion of the polycyclohexylbenzenes to additional monocyclohexylbenzene is effected by dealkylation. Dealkylation or cracking is also typically effected in a reactor separate from the hydroalkylation reactor, such as a reactive distillation unit, at a temperature of about 150° C. to about 500° C. and a pressure of 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 to 3550 kPa), a weight hourly space velocity of about 0.2 to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

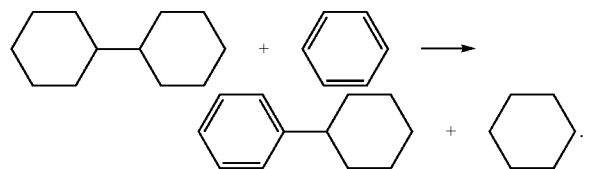

The catalytic treatment can be conducted on the direct product of the hydroalkylation reaction or after distillation of the hydroalkylation reaction product to separate the $C_6$ and/or the heavies fraction.

The cyclohexylbenzene-rich stream separated from the hydroalkylation reaction product is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is normally conducted in the presence of a cyclic imide catalyst. Suitable catalysts comprise an imide group having the following formula I:

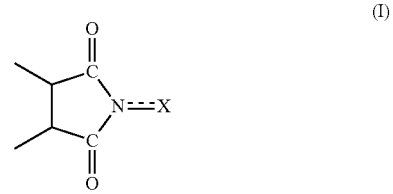

wherein X represents an oxygen atom, a hydroxyl group, or an acyloxy group.

Generally, the cyclic imide catalyst obeys the general formula II:

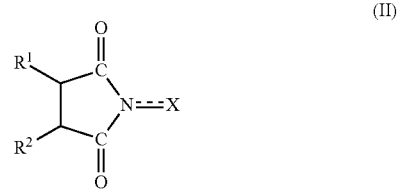

wherein X represents an oxygen atom, a hydroxyl group, or an acyloxy group and $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may bound together to form a double bond or an aromatic- or non-aromatic ring.

More specifically, the cyclic imide employed as the oxidation catalyst typically obeys the general formula III:

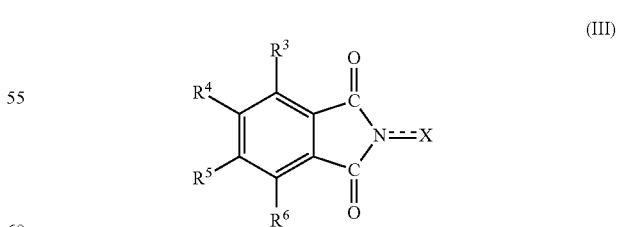

wherein X represents an oxygen atom, a hydroxyl group and each of $R^3$, $R^4$, $R^5$, and $R^6$ is independently selected from H, aliphatic or aromatic alkoxy radical, carboxyl radical, alkoxy-carbonyl radical or hydrocarbon radical, each of which has 1 to 20 carbon atoms, $SO_3H$, $NH_2$, OH, F, Cl, Br, I and/or $NO_2$.

In one practical embodiment, the cyclic imide catalyst comprises N-hydroxyphthalimide.

The cyclic imide oxidation catalyst can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the heat of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Purification of the Oxidation Product

Typically, the product of the cyclohexylbenzene oxidation reaction contains at least 5 wt %, such as at least 10 wt %, for example at least 15 wt %, or at least 20 wt % cyclohexylbenzene hydroperoxide based upon the total weight of the oxidation reaction effluent. Generally, the oxidation reaction effluent contains no greater than 50 wt %, or no greater than 40 wt %, or no greater than 30 wt %, or no greater than 25 wt % of cyclohexylbenzene hydroperoxide based upon the total weight of the oxidation reaction effluent. The oxidation reaction effluent further comprises imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

In accordance with the present process, at least a portion of the oxidation reaction effluent is subjected to purification to remove at least part of any imide catalyst and the unreacted cyclohexylbenzene before passage to the cleavage step. In various embodiments, at least 70% of the catalyst is removed, or at least 80%, or at least 90%, or substantially all of the catalyst is removed. In particular, all or a fraction of the oxidation reaction effluent normally undergoes initial treatment to reduce the level of the cyclic imide in the effluent to, for example, less than 100 ppmw, such as less than 20 ppmw. This is conveniently effected by contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. Another possible separation involves passage of all or a fraction of the oxidation effluent over a bed of solid sorbent. Suitable solid sorbents include alkali metal carbonates, alkali metal bicarbonates, alkali metal hydroxides, alkali metal hydroxide-carbonate complexes, alkaline earth metal carbonates, alkaline earth metal bicarbonates, alkaline earth metal hydroxides, and alkaline earth metal hydroxide-carbonate complexes. An example of separation of cyclic imide by basic material treatment is disclosed in International Patent Publication No. WO 2009/025939.

After treatment to remove the cyclic imide catalyst, the oxidation effluent is maintained under conditions such that crystals of cyclohexylbenzene hydroperoxide form and separate from the treated reaction product. This is conveniently achieved by cooling the reaction product and allowing the crystals to form. For example, the treated reaction product may be cooled to a temperature between about 1° C. to about 15° C., or about 2° C. and about 10° C., or about 3° C. to about 9° C., or about 4° C. to about 8° C., or about 5° C. and allowing the crystals to form, which is normally takes from about 2 hours to about 170 hours. When crystallization is complete the cyclohexylbenzene hydroperoxide crystals can be recovered from the oxidation effluent and supplied to the cleavage step. In one embodiment, "recovering" the crystals means separating at least a portion of the crystals from the oxidation effluent. The crystallization step can be performed one time or can be repeated several times to improve the yield of the cyclohexylbenzene hydroperoxide. The recovered cyclohexylbenzene hydroperoxide crystals typically have a purity of >85%, preferably >90%.

After recovery of the cyclohexylbenzene hydroperoxide, the remainder of the oxidation effluent, which will be rich in unreacted cyclohexylbenzene, can be recycled to the oxidation step. This effluent will also contain some cyclohexylbenzene hydroperoxide which will help to dissolve NHPI in this solution and also initiate the free radical chemistry and improve the reaction rate.

In one embodiment, the cyclohexylbenzene hydroperoxide crystals can be used in epoxidation of one or more olefins.

Hydroperoxide Cleavage

The final reactive step in the conversion of the cyclohexylbenzene into phenol and cyclohexanone involves the acid-catalyzed cleavage of the cyclohexylbenzene hydroperoxide recovered from the oxidation reaction effluent (e.g., the cyclohexylbenzene hydroperoxide crystals).

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Both Brønsted acids and Lewis acids can be used. Suitable acid catalysts include, but are not limited to, sulfuric acid, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

Suitable cleavage conditions include a temperature of at least 20° C. and no greater than 200° C., or at least 40° C. and no greater than 120° C., and a pressure of at least 1 and no greater than 370 psig (at least 7 and no greater than 2,550 kPa, gauge), or at least 14.5 and no greater than 145 psig (at least 100 and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction are phenol and cyclohexanone, each of which generally comprise about 40 to about 60 wt %, or about 45 to about 55 wt % of the cleavage reaction product, such wt % based on the weight of the cleavage reaction product exclusive of unreacted cyclohexylbenzene and acid catalyst.

The cleavage reaction product also typically contains unreacted acid catalyst and hence at least a portion of the cleavage reaction product is normally neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium and radium; an oxide of Group III of the Periodic Table of Elements treated with a metal selected from lithium, potassium, sodium, rubidium and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5°

C., or 10° C., or 15° C., or 20° C., or 30° C., or 40° C. lower than the temperature of the cleavage reaction.

Suitable neutralization conditions may include a pressure of about 1 to about 500 psig (5 kPa to 3450 kPa, gauge), or about 10 to 200 psig (70 to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which can be purified and separated by methods well known in the art.

The invention will now be more particularly described with reference to the following non-limiting Examples.

Example 1

Oxidation of CHB in the Presence of NHPI 150.04 g of cyclohexylbenzene (CHB) and 0.161 g of N-hydroxyphthalimide (NHPI) were loaded into a 300-mL autoclave and the autoclave was heated to 110° C. under flowing $N_2$. The $N_2$ flow was then turned off and an air flow turned on (250 cc/min) with vigorous stirring (1000 rpm); and the autoclave was heated at 110° C. for 7 hr. The autoclave was then allowed to cool down to room temperature under $N_2$ and the contents collected as the oxidation products.

Example 2

Removing NHPI from the CHB Oxidation Products

The CHB oxidation products generated in a fashion similar to that in Example 1 were combined (3007.5 g) and washed with 1% $Na_2CO_3$ aqueous solution (3×460 mL), followed by water wash, and the organic phase separated. The pale yellow organic phase (2756.6 g) was dried over 275.7 g anhydrous $MgSO_4$ to remove residual water. The NHPI level in the final washed product is <10 ppm, compared to 679 ppm in the un-washed sample.

Example 3

Crystallization of CHBHP from the Oxidation Products

After the NHPI was removed, the CHB oxidation products from Example 2 were divided into 500-mL portions and put into 1-liter plastic bottles. The bottles were placed in a refrigerator held at 5° C. White crystals of cyclohexylbenzene hydroperoxide (CHBHP) started to grow in two (2) days. The samples were allowed to sit in the refrigerator for a week. The mother liquor was decanted; and solid CHBHP crystals were washed with pentane and dried under $N_2$. Yield of solid CHBHP is 44 g. GC analysis of the CHBHP crystal reveals a purity of 96%. The CHBHP concentration in the mother liquor after the crystallization is 10.5%, compared to 19.3% before crystallization. More CHBHP crystals grew from the mother liquor upon further sitting at 5° C.

For comparison, no CHBHP crystallization occurs if NHPI is not removed from the oxidation products. For example, a sample the same oxidation products, which was not subjected to the washing steps of Example 2, did not yield any CHBHP crystal even after being stored in the refrigerator for two months at 5° C.

Example 4

Cleavage of High Purity CHBHP Using Sulfuric Acid

An amount of 4.61 g of high purity CHBHP as described in Example 3 was dissolved in 12.85 g of acetone to make a stock solution. The acetone solution was reacted with 10000 ppm of sulfuric acid in a 5 cc jacketed glass CSTR reactor fitted with a circulating temperature bath. At the steady state, a residence time of 5 min and a temperature of 54° C. were achieved. A 1-cc aliquot sample was taken at steady state, neutralized with 10% $Na_2CO_3$ solution, and analyzed by GC. High yields to phenol and cyclohexanone are achieved (Table 1).

TABLE 1

Cleavage products from high purity CHBHP using sulfuric acid

| Component | Feed (wt %) | Product (wt %) |
|---|---|---|
| cyclohexanone | 0.05 | 47.25 |
| phenol | 0.04 | 45.31 |
| CHB | 2.24 | 2.21 |
| Phenyl-1-cyclohexene | 0.15 | 0.50 |
| 4-Phenyl-cyclohexanol | 0.39 | 0.23 |
| 1-Phenyl-cyclohexanol | 0.50 | 0.00 |
| Phenyl-3-cyclohexene | 0.04 | 0.41 |
| CHBHP | 95.83 | 0.00 |
| Other Peroxides | 0.16 | 0.00 |
| 6-hydroxy-hexanophenone | 0.24 | 3.98 |
| CHBHP conv. (%) | | 100.00 |
| Cyclohexanone yield (%) | | 98.02 |
| Phenol yield (%) | | 97.98 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexylbenzene hydroperoxide, the process comprising:
   (a) contacting cyclohexylbenzene with oxygen and N-hydroxyphthalimide to produce a reaction product comprising cyclohexylbenzene hydroperoxide and at least a portion of the N-hydroxyphthalimide;
   (a-1) removing at least a portion of the N-hydroxyphthalimide from the reaction product;
   (b) after the removing (a-1), treating at least a portion of the reaction product under conditions such that crystals of cyclohexylbenzene hydroperoxide form; and
   (c) recovering at least a portion of the cyclohexylbenzene hydroperoxide crystals from the reaction product.

2. The process of claim 1, wherein at least a portion of the reaction product is treated with an aqueous solution of a base upstream of the treating step (b) to remove at least part of the N-hydroxyphthalimide from the reaction product.

3. The process of claim 2, wherein the base is a metal carbonate and/or hydrogen carbonate.

4. The process of claim 1, wherein the reaction product is treated with a solid sorbent upstream of the treating step (b) to remove at least part of the N-hydroxyphthalimide from the reaction product.

5. The process of claim 4, wherein the solid sorbent is selected from alkali metal carbonates, alkali metal bicarbonates, alkali metal hydroxides, alkali metal hydroxide-carbonate complexes, alkaline earth metal carbonates, alkaline earth metal bicarbonates, alkaline earth metal hydroxides, and alkaline earth metal hydroxide-carbonate complexes.

6. The process of claim 1, wherein the conditions in (b) comprise cooling the reaction product to a temperature sufficient to form at least some cyclohexylbenzene hydroperoxide crystals.

7. The process of claim 1, wherein the conditions in (b) comprise cooling the reaction product to a temperature between about 2° C. and about 10° C.

8. The process of claim 1, wherein (b) and (c) are repeated a plurality of times.

9. The process of claim 1, wherein the reaction product comprises at least 5 wt % of cyclohexylbenzene hydroperoxide, based upon total weight of the reaction product.

10. The process of claim 1, wherein the cyclohexylbenzene hydroperoxide crystals have a purity of greater than 85%.

11. The process of claim 1, and further comprising recycling at least a portion of the reaction product remaining after recovery of the cyclohexylbenzene hydroperoxide crystals to the contacting step (a).

12. The process of claim 1, wherein the reaction product formed in the contacting step (a) further comprises unreacted cyclohexylbenzene.

13. The process of claim 1, and further comprising using the cyclohexylbenzene hydroperoxide recovered in the recovering step (c) as an oxidant or as an initiator.

14. A process for producing phenol and cyclohexanone, the process comprising:
  (a) contacting cyclohexylbenzene with oxygen and N-hydroxyphthalamide to produce a reaction product comprising cyclohexylbenzene hydroperoxide and at least a portion of the N-hydroxyphthalamide;
  (a-1) treating the reaction product to remove at least a portion of the N-hydroxyphthalimide prior to the treating step (b)
  (b) after the treating (a-1), treating at least a portion of the reaction product under conditions such that crystals of cyclohexylbenzene hydroperoxide form;
  (c) recovering at least a portion of the cyclohexylbenzene hydroperoxide crystals from the reaction product; and
  (d) cleaving at least some of the cyclohexylbenzene hydroperoxide recovered in (c) to produce phenol and cyclohexanone.

15. The process of claim 14, wherein the reaction product is treated with an aqueous solution of a base to remove at least a portion of the N-hydroxyphthalimide.

16. The process of claim 14, wherein the reaction product is treated with a solid sorbent to remove at least a portion of the N-hydroxyphthalimide.

17. The process of claim 16, wherein the solid sorbent is selected from alkali metal carbonates, alkali metal bicarbonates, alkali metal hydroxides, alkali metal hydroxide-carbonate complexes, alkaline earth metal carbonates, alkaline earth metal bicarbonates, alkaline earth metal hydroxides, and alkaline earth metal hydroxide-carbonate complexes.

18. The process of claim 14, wherein the treating step (b) comprises cooling the reaction product to a temperature sufficient to form at least some cyclohexylbenzene hydroperoxide crystals.

19. The process of claim 14, wherein the treating step (b) comprises cooling the reaction product to a temperature between about 2° C. and about 10° C.

20. The process of claim 14, wherein at least a portion of the cyclohexylbenzene hydroperoxide crystals are dissolved in a solvent prior to the cleaving step (d).

21. The process of claim 20, wherein the solvent is acetone.

\* \* \* \* \*